(12) United States Patent
Jun

(10) Patent No.: US 9,833,282 B2
(45) Date of Patent: Dec. 5, 2017

(54) ELECTRODE FOR RADIOFREQUENCY TISSUE ABLATION

(76) Inventor: Myong-Ki Jun, Gwacheon-Shi (KR)

(*) Notice: Subject to any disclaimer, the term of this patent is extended or adjusted under 35 U.S.C. 154(b) by 969 days.

(21) Appl. No.: 12/465,843

(22) Filed: May 14, 2009

(65) Prior Publication Data
US 2009/0287206 A1    Nov. 19, 2009

(30) Foreign Application Priority Data
May 15, 2008  (KR) .................. 10-2008-0045213

(51) Int. Cl.
  A61B 18/14    (2006.01)
  A61B 18/16    (2006.01)
  A61B 18/00    (2006.01)
  A61B 18/12    (2006.01)

(52) U.S. Cl.
  CPC .......... *A61B 18/1477* (2013.01); *A61B 18/16* (2013.01); *A61B 2018/00029* (2013.01); *A61B 2018/00083* (2013.01); *A61B 2018/1253* (2013.01); *A61B 2018/1425* (2013.01); *A61B 2218/002* (2013.01)

(58) Field of Classification Search
  CPC .. A61B 2018/0281; A61B 2018/00035; A61B 2018/0293; A61B 2018/0268
  USPC .................. 606/29, 32, 34, 41; 607/98, 115; 604/113
  See application file for complete search history.

(56) References Cited

U.S. PATENT DOCUMENTS 5,423,807 A * 6/1995 Milder ........................... 606/20
5,688,267 A * 11/1997 Panescu et al. ............... 606/41
5,697,927 A * 12/1997 Imran et al. .................... 606/41
6,210,411 B1 * 4/2001 Hofmann et al. .............. 606/52
6,241,666 B1 * 6/2001 Pomeranz et al. ............ 600/381
6,506,189 B1   1/2003 Rittman, III et al.
6,514,251 B1 * 2/2003 Ni et al. .......................... 606/41
(Continued)

FOREIGN PATENT DOCUMENTS

EP     0956826 A2     11/1999
JP     11-505747       5/1999
(Continued)

OTHER PUBLICATIONS

Chinese Office Action dated Jun. 2, 2010 in corresponding Chinese Patent Application 200910137582.7 and an English-language translation.
(Continued)

*Primary Examiner* — Thomas Giuliani
(74) *Attorney, Agent, or Firm* — Mintz Levin Cohn Ferris Glovsky and Popeo, P.C.; Steven M. Jensen

(57) ABSTRACT

An electrode for an electrosurgical unit is used for ablating and necrosing a living tissue by RF electric energy. The electrode can be a hollow electrode formed in an elongated hollow tube shape, including a non-insulating region of a predetermined length formed on one side, and an insulating region formed on an outer surface other than the non-insulating region. The electrode further can include a saline solution circulation structure that supplies pressurized saline solution for cooling a living tissue which is in contact with the hollow electrode from the outside of the living tissue to the inside of the hollow electrode, and one or more saline solution discharge holes formed in the non-insulating region of the hollow electrode to discharge some of the circulating pressurized saline solution to the living tissue.

8 Claims, 5 Drawing Sheets

(56) References Cited

U.S. PATENT DOCUMENTS

| 2005/0171526 A1* | 8/2005 | Rioux et al. ............ 606/41 |
| 2006/0122593 A1* | 6/2006 | Jun ............ A61B 18/1477 606/41 |
| 2009/0177193 A1* | 7/2009 | Wang et al. ............ 606/33 |

FOREIGN PATENT DOCUMENTS

| JP | 2002-522182 | 7/2002 |
| JP | 2006-524063 | 10/2006 |
| WO | 2004093704 A1 | 11/2004 |

OTHER PUBLICATIONS

Office Action dated Jun. 20, 2011 and English-language translation for Japanese Patent Application 2009-117272.

Office Action dated Nov. 22, 2011 in corresponding Japanese Application 2009-117272, and English-language translation.

Y. Miao, et al., "A Comparative Study on Validation of a Novel Cooled-Wet Electrode for Radiofrequency Liver Ablation," Investigative Radiology, vol. 35, Issue 7, Jul. 2000, pp. 438-444.

J. Cha, et al., "Radiofrequency Ablation Zones in Ex Vivo Bovine and In Vivo Porcine Livers: Comparison of the Use of Internally Cooled Electrodes and Internally Cooled Wet Electrodes," Cardiovascular and Interventional Radiological Society of Europe (CIRSE), Apr. 2009.

J. Kim, et al., "Percutaneous Radiofrequency Ablation Using Internally Cooled Wet Electrodes for the Treatment of Hepatocellular Carcinoma," AJR, Feb. 2012, pp. 471-476.

H. Yoon, et al., "Percutaneous radiofrequency ablation using internally cooled wet electrodes for treatment of colorectal liver metastases," Clinical Radiology, Feb. 2012, pp. 122-127.

Y. Lee and J. Byun, "Bipolar Radiofrequency Ablation Using Dual Internally Cooled Wet Electrodes: Experimental Study in Ex Vivo Bovine Liver," J. Korean Society of Radiology, 67(6), Dec. 2012, pp. 425-431.

Mi-Hyun Park, et al., "Comparison of Internally Cooled Wet Electrode and Hepatic Vascular Inflow Occlusion Method for Hepatic Radiofrequency Ablation," Gut and Liver, vol. 6, No. 4, Oct. 2012, pp. 471-475.

H. Kim, "A comparison of radiofrequency ablation between thyroid-dedicated internally cooled wet electrodes and internally cooled electrodes: an experimental study in ex vivo bovine liver," University of Ulsan Department of Medicine, Doctoral Thesis, Feb. 2013.

J. Kim, et al., "Percutaneous Radiofrequency Ablation with Internally Cooled versus Internally Cooled Wet Electrodes for Small Subphrenic Hepatocellular Carcinomas," JVIR, Mar. 2013.

J. Kim, et al., "Percutaneous radiofrequency ablation with internally cooled wet electrodes versus cluster electrodes for the treatment of single medium-sized hepatocellular carcinoma," Society of Gastrointestinal Intervention, Sep. 2014, pp. 98-103.

J. Yoon, et al., "Switching bipolar hepatic radiofrequency ablation using internally cooled wet electrodes: comparison with consecutive monopolar and switching monopolar modes," The British Journal of Radiology, Jun. 2015.

\* cited by examiner

ELECTRODE FOR RADIOFREQUENCY TISSUE ABLATION

BACKGROUND OF THE INVENTION

1. Field of the Invention

The present invention relates to an electrode for an electrosurgical unit, and more particularly to, an electrode for an electrosurgical unit for the use in ablating and necrosing a living tissue by RF electric energy.

2. Description of the Related Art

A technique for piercing and inserting a long hollow tube-shaped electrode into a target living tissue and ablating (or coagulating) the living tissue by RF energy has been publicly known. In this case, when a current flows into the living tissue, the living tissue is heated, so that the living tissue and blood vessels are ablated by a more or less complicated biochemical mechanism. Such a process depends on ablation of a cell caused by thermal deformation of proteins in the cell over about 60° C. Here, the cell includes the tissue, blood vessel and blood. However, this technique has a problem in that the living tissue and blood around the electrode are excessively ablated and carbonized, and the carbonized living tissue around the electrode operates as an insulator which prevents extension of an ablation region of the living tissue.

In order to solve the foregoing problem, U.S. Pat. No. 6,210,411 discloses a technique for supplying saline solution through the inside of a hollow tube of an electrode, and discharging the saline solution to the outside via a porous body formed around a tip portion of the electrode. Like the above patent, techniques for discharging saline solution to the outside of an electrode prevent carbonization of a living tissue adjacent to the electrode by vaporization latent heat of the saline solution, and makes the saline solution soak into capillary vessels of the tissue around the electrode, to thereby improve electric conductivity and extend an ablation region of the living tissue. However, when a flow rate of the saline solution which can be infused into the living tissue increases, it has a detrimental effect on a patient. Therefore, since the flow rate of the saline solution which can be infused into the living tissue is restricted, if RF energy applied to the living tissue exceeds a limit point, carbonization of the tissue occurs around the electrode. As a result, this method also has a limit in extending an ablation region.

In addition, U.S. Pat. No. 6,506,189 discloses a technique for installing a saline solution tube in a hollow tube-shaped electrode with a closed tip portion, the saline solution tube having a smaller diameter than that of the electrode, and cooling the electrode by saline solution circulation that introduces saline solution into the inside of the electrode through the inside of the saline solution tube, makes the saline solution exchange heat in the electrode, and collects the saline solution through a space between the saline solution tube and the electrode. When RF energy is applied via the electrode, the nearest tissue to the electrode is mostly heated and possibly carbonized. As the electrode is water-cooled, the nearest tissue which is in contact with the electrode can be cooled and prevented from carbonization. Accordingly, it is possible to extend an ablation region of the living tissue. However, if RF energy applied to the living tissue exceeds a limit point, carbonization of the tissue occurs around the electrode. Consequently, this method also has a limit in extending the ablation region.

The aforementioned methods have been known as forming a spherical ablation region having a radius of about 2 cm from an electrode.

Meanwhile, Korean Laid-Open Patent No. 10-2004-0092614 filed by the present applicant suggests an electrode construction including a hollow electrode formed in a hollow tube shape with a mechanically-bored hole, a saline solution tube for introducing pressurized saline solution into the inside of the hollow electrode, and a flow control means for controlling a flow rate of saline solution discharged via the hole of the hollow electrode. According to the above patent, the pressurized saline solution flows from the outside of a living tissue to the inside of the hollow electrode through the saline solution tube, and cools the hollow electrode. The heat-exchanged saline solution is discharged to the outside of the living tissue, and some of the pressurized saline solution is discharged via the hole bored in the hollow electrode. A sheath tube having a hole bored alternately with the hole of the hollow electrode is covered on the hollow electrode, which prevents the pressurized saline solution from being emitted explosively to the outside of the living tissue. However, since it is difficult to couple the separate flow control means to the hollow electrode, there is an economical disadvantage. In addition, when the electrode inserted into the body is taken out, the flow control means may be separated therefrom. Moreover, the sheath tube may reduce a cooling effect of the pressurized saline solution. Further, since a diameter of the overall electrode, i.e. a thickness of a needle increases, when the electrode is inserted into the body, it causes severe bleeding.

SUMMARY OF THE INVENTION

Therefore, an object of the present invention is to provide an economical and very simple electrode structure, wherein pressurized saline solution can sufficiently cool the inside of a hollow electrode, and can be discharged from the hollow electrode to the inside of a living tissue which is in contact with the hollow electrode as much as necessary.

According to an aspect of the present invention, there is provided an electrode for an electrosurgical unit, including: a hollow electrode formed in an elongated hollow tube shape, a non-insulating region of a predetermined length being formed on one side of which, an insulating region being formed on an outer surface of which other than the non-insulating region; a saline solution circulation structure that supplies pressurized saline solution for cooling a living tissue which is in contact with the hollow electrode from the outside of the living tissue to the inside of the hollow electrode, and discharges the pressurized saline solution from the inside of the hollow electrode to the outside of the living tissue; and one or more saline solution discharge holes formed in the non-insulating region of the hollow electrode to discharge some of the circulating pressurized saline solution to the living tissue which is in contact with the hollow electrode.

Here, the saline solution discharge hole may be formed in a plural number in positions symmetrical about the hollow electrode.

In addition, in a state where the hollow electrode is exposed in an air, less than 5% of the pressurized saline solution circulating in the hollow electrode may be discharged to the air via the saline solution discharge hole, preferably, 0.3 to 3.8% of the pressurized saline solution circulating in the hollow electrode may be discharged to the air via the saline solution discharge hole, and more preferably, 0.9 to 2.0% of the pressurized saline solution circulating in the hollow electrode may be discharged to the air via the saline solution discharge hole.

Alternately, in a state where the hollow electrode is exposed in an air, when the saline solution circulates in the electrode at 90 cc/min., preferably, a flow rate of the saline solution discharged to the air via the saline solution discharge hole ranges from 0.31 to 3.42 cc/min.

Moreover, in a state where the hollow electrode is exposed in the air, when the saline solution circulates in the electrode at 90 cc/min., more preferably, a flow rate of the saline solution discharged to the air via the saline solution discharge hole ranges from 0.82 to 1.65 cc/min.

Alternately, preferably, a radius of the saline solution discharge hole ranges from 0.01 to 0.025 mm.

Further, more preferably, a radius of the saline solution discharge hole ranges from 0.0125 to 0.0175 mm.

Furthermore, preferably, the pressurized saline solution is pressurized to 700 to 1060 KPa, and supplied to the inside of the hollow electrode.

According to the present invention, since cooling in the hollow electrode can be maximized economically and the saline solution can be discharged at a fixed flow rate to the inside of the living tissue which is in contact with the hollow electrode, it is possible to easily extend an ablation necrosis region of the living tissue.

In addition, the electrode can minimize bleeding, and can be easily applied to a doctor's operation.

BRIEF DESCRIPTION OF THE DRAWINGS

The above and other objects, features and advantages of the present invention will become apparent from the following description of a preferred embodiment given in conjunction with the accompanying drawings, in which.

DESCRIPTION OF THE PREFERRED EMBODIMENT

Although the present invention has been described in detail in connection with the accompanying drawings and the embodiments, the scope of the invention is not limited thereto, but is defined by the appended claims.

Figure 1:
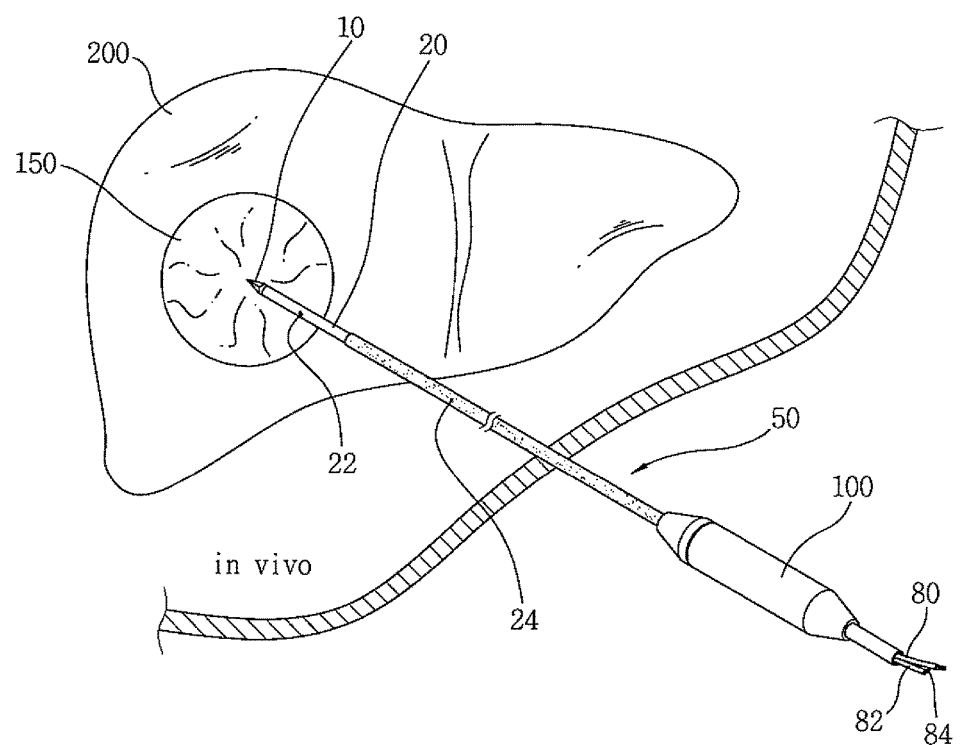
FIG. 1 is a view illustrating an electrode for an electrosurgical unit, a saline solution discharge hole being bored in an outer surface of the electrode.

FIG. 1 schematically shows a state where a hollow electrode 50 formed in an elongated hollow tube shape according to the present invention, a non-insulating region 20 of a predetermined length being formed on one side of which, an insulating region 24 being formed on an outer surface of which other than the non-insulating region 20, is inserted into a living tissue to perform ablation and necrosis. A closed tip-portion 10 on one side of the hollow electrode 50 is formed in the shape of a pointed end member. When the closed tip portion 10 on its one side is formed integrally with the hollow electrode 50, it is easy to pierce and insert the hollow electrode 50 into a living tissue 200 such as the liver. As illustrated in FIG. 1, a saline solution discharge hole 22 is formed in the non-insulating region 20 of the hollow electrode 50. In a state where the hollow electrode 50 is inserted into a tumor tissue in the living tissue, when the hollow electrode 50 is applied with an RF current, ablation and necrosis proceed in an approximately spherical shape. A region where ablation and necrosis have proceeded is indicated by reference numeral 150 in FIG. 1. For example, when a liver cancer is found in the liver, the operation is performed to form a spherical ablation necrosis region larger than a liver cancer tissue.

That is, ablation and necrosis occur in the living tissue 200 by heating. To this end, when the non-insulating region 20 is made to contact the tumor tissue and applied with an RF current via a line 80, since the non-insulating region 20 is a conductor, the RF current flows into the living tissue 200 which is in contact with the non-insulating region 20, performing ablation and necrosis to a certain range. In order to prevent ablation and necrosis of a unwanted body portion, most of the hollow electrode 50 other than the non-insulating region 20 is insulation-coated or covered with a rubber tube to form the insulating region 24. That is, when the closed tip portion 10 is put over the tumor tissue and an RF current is applied thereto, the RF current flows into the tissue which is in contact with the non-insulating region 20, so that ablation and necrosis occur in an approximately spherical shape around the closed tip portion 10. If a diameter of the hollow electrode 50 exceeds 3 mm, when the hollow electrode 50 is pierced and inserted into the skin, bleeding is severe, which makes an operation difficult. Therefore, preferably, the diameter of the hollow electrode 50 does not exceed 3 mm. So as to minimize bleeding, more preferably, the diameter of the hollow electrode 50 is equal to or smaller than 2 mm or 1.5 mm.

Meanwhile, the living tissue 200 and blood around the non-insulating region 20 of the hollow electrode 50 are excessively ablated and carbonized, and the carbonized living tissue 200 around the electrode 50 operates as an insulator which prevents extension of an ablation region of the living tissue 200. Accordingly, the present invention provides a saline solution circulation structure that performs cooling of the hollow electrode 50 and the living tissue 200. To this end, the hollow electrode 50 is formed in a hollow tube shape, and a saline solution tube 30 is located therein to supply saline solution to the hollow electrode 50. The saline solution may be supplied through the saline solution tube 30 and discharged through a space between the saline solution tube 30 and the hollow electrode 50, and vice versa. Since the hollow electrode 50 is very thin due to the aforementioned reason, the saline solution introduced into the inside of the hollow electrode 50 through the saline solution tube 30 flows into the inside of the hollow electrode 50 inevitably in a very high pressure state (pressurized into a high pressure of about 700 to 1060 KPa), cools the non-insulating region 20, an inner surface of the hollow electrode 50 and the closed tip portion 10, and is returned and discharged.

The saline solution is introduced from the outside through the saline solution tube 30, and exchanges heat in the non-insulating region 20 of the hollow electrode 50. The heat-exchanged saline solution is discharged to the outside through the space between the hollow electrode 50 and the saline solution tube 30 (may be reverse as mentioned above). That is, referring to FIG. 2, the saline solution introduced through a supply duct 82 passes through the inside of an electrode handle 100, and flows into the inside of the hollow electrode 50 through the saline solution tube 30. After heat exchange, the saline solution is taken out of the body through the space between the hollow electrode 50 and the saline solution tube 30, and discharged through a discharge duct 84 via the electrode handle 100.

In addition, according to the present invention, in order to prevent excessive ablation and carbonization by vaporization latent heat and improve electric conductivity by using pressurized saline solution as a cooling fluid of the hollow electrode 50 and discharging some of the pressurized saline solution to the inside of the living tissue 200, the saline solution discharge hole 22 is formed in the non-insulating region 20 of the hollow electrode 50. If the hole 22 is too big, since the circulating saline solution has a very high pressure, the pressurized saline solution may be emitted explosively, damaging an organ of the body, and preventing the non-insulating region 20 and the closed tip portion 10 of the hollow electrode 50 from being located in a target tumor tissue point. Moreover, since an allowable flow rate of saline solution infused into the body during an operation is generally equal to or less than about 120 cc/hr., a flow rate of saline solution emitted into the body should be strictly controlled. However, it is necessary to consider a flow rate of saline solution vaporized with application of an RF current.

The most remarkable characteristic of the present invention is to provide a structure wherein cooling of the non-insulating region 20 and the closed tip portion 10 can be efficiently performed by pressurized saline solution during an operation, and some of the pressurized saline solution for cooling can be efficiently discharged to the inside of the living tissue 200.

For example, the hole 22 may be bored by a laser using ND:YAG:$CO_2$ as a source. The laser can bore a micro hole that cannot be formed by a mechanical method. The hole is bored mainly in a circular shape. However, the shape of the hole is irrelevant. Factors for controlling a flow rate of saline solution are the size of the hole and the flow rate of the circulating pressurized saline solution.

According to the present invention, since it is not necessary to install a special flow control means on the outside of the hollow electrode 50, it is possible to manufacture a hollow electrode with a diameter equal to or smaller than 1.5 mm. Therefore, bleeding is minimized during an operation, which lightens a burden of a doctor conducting the operation. However, if the diameter of the overall electrode is less than 1.2 mm, even though the electrode is manufactured with a minimum thickness to be pierced and inserted into the body without damage, the current technology cannot dispose a temperature sensor therein and circulate pressurized saline solution therein. Accordingly, taking bleeding possibility into consideration, the diameter of the hollow electrode 50 ranges from 1.2 mm to 3.0 mm, preferably ranges from 1.2 mm to 2.0 mm, and more preferably ranges from 1.2 mm to 1.5 mm.

Figure 2:
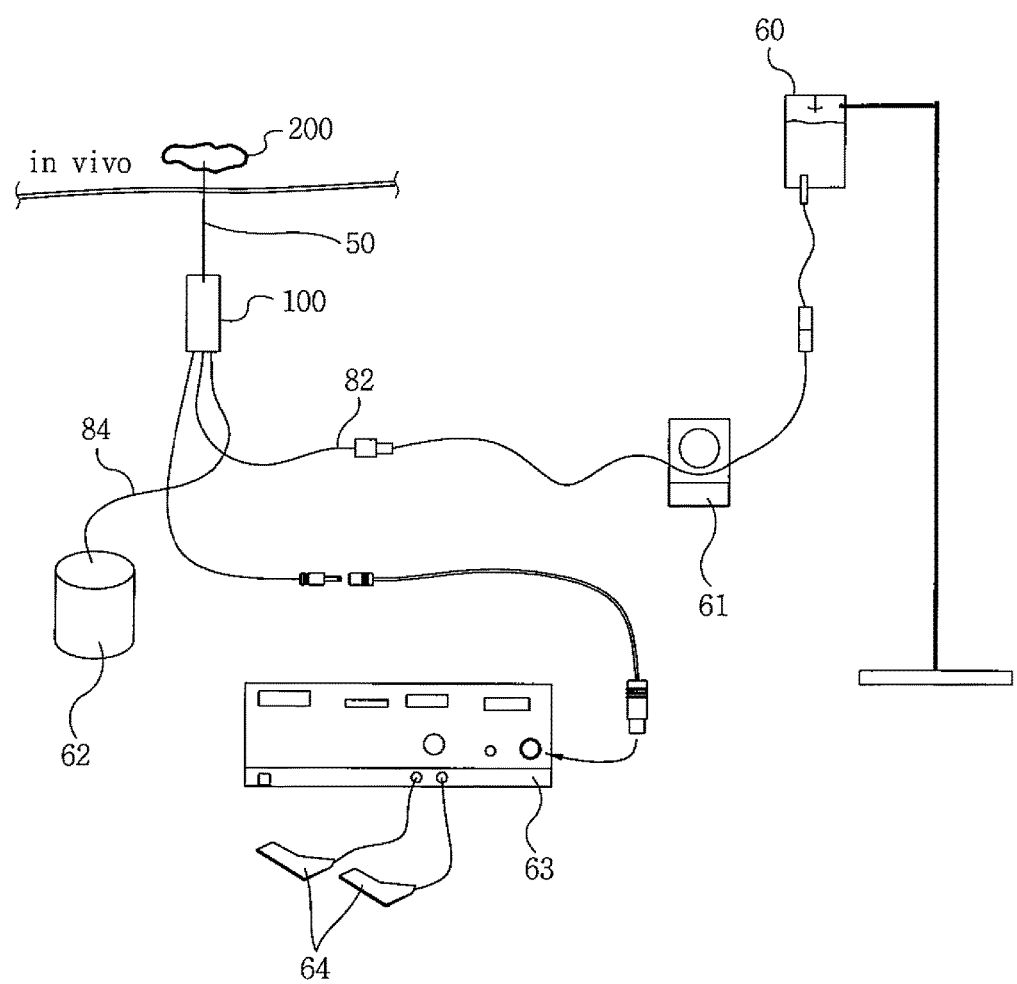
FIG. 2 is a schematic view illustrating an overall operation equipment including the electrode of FIG. 1.

FIG. 2 is a schematic view illustrating an overall operation equipment including the hollow electrode 50 of FIG. 1 and the saline solution circulation structure.

The overall system includes the hollow electrode 50, the saline solution circulation structure such as a saline solution infusion pump 61 which can transfer saline solution to the saline solution tube 30 inside the electrode 50 through the supply duct 82 at a certain flow rate or pressure, or a discharged saline solution storage unit 62 which stores the saline solution discharged to the outside of the electrode 50 through the discharge duct 84 after cooling the electrode 50, and an RF generator 63 for applying an RF current to the non-insulating region 20 of the hollow electrode 50 which is in contact with the living tissue 200. A plurality of return pads 64 are electrically connected to the RF generator 63.

The return pads 64 are attached to e.g. the inside of a thigh of the body during an operation. The electrode 50 is inserted into the living tissue 200, e.g. the liver in the body. Here, slight bleeding may occur. After the electrode 50 is inserted into the living tissue 200, the RF generator 63 applies an appropriate RF (e.g., pulse) to the electrode 50, so that the living tissue 200 is heated by the electrode 50, and ablated and necrosed. In this process, the living tissue 200 around the electrode 50 may be carbonized, operating as an insulator which prevents extension of an ablation region of the living tissue 200. So as to prevent this, saline solution, particularly, saline solution supplied from a physiologic saline solution bag 60 is pressurized to a certain pressure or flow rate via the saline solution infusion pump 61, and supplied to the inside of the hollow electrode 50 through the supply duct 82 and the saline solution tube 30.

Figure 3:
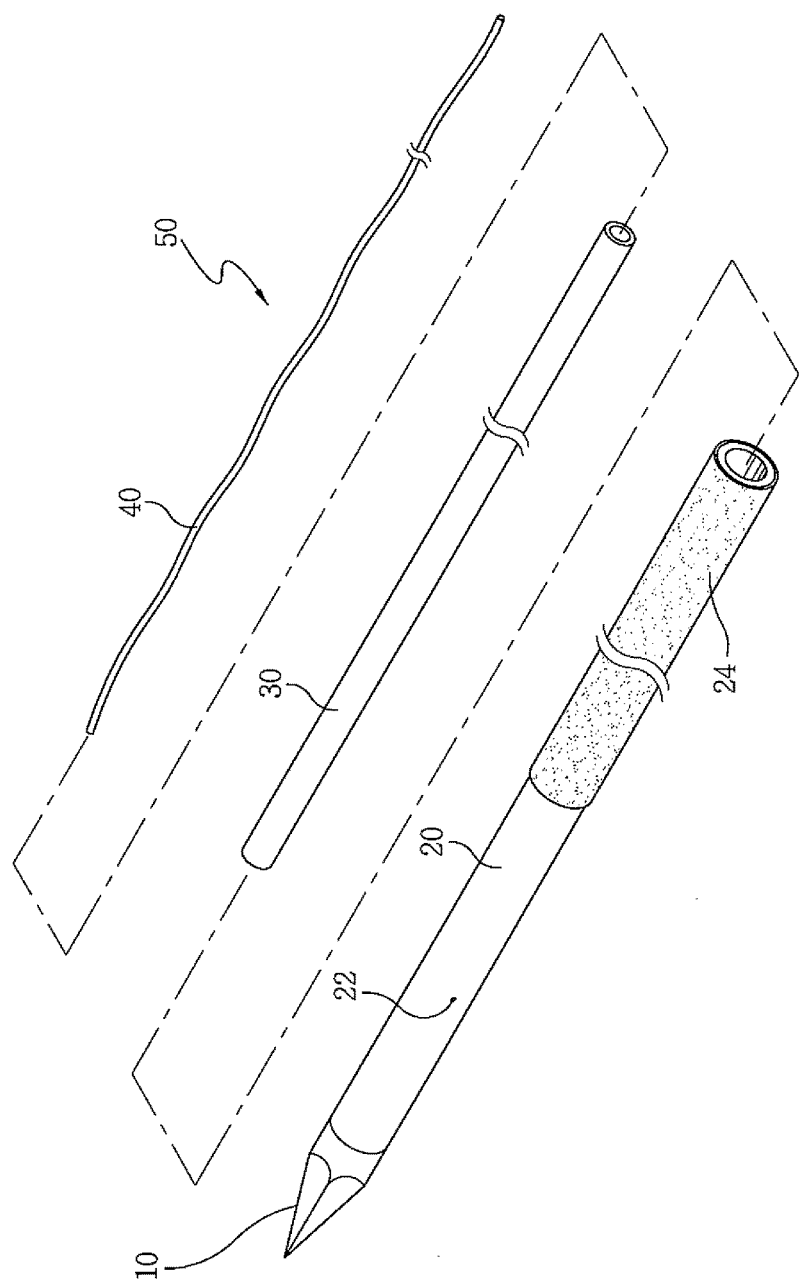
FIG. 3 is a view illustrating a construction of an electrode and a saline solution tube.

FIG. 3 is an exploded perspective view illustrating components of the hollow electrode 50, particularly, a detailed construction of the non-insulating region 20, the saline solution discharge hole 22, the insulating region 24, the saline solution tube 30 and a temperature sensor line 40. A pointed end member which is the closed tip portion 10 is formed integrally with the hollow electrode 50. That is, a filled conductive pointed end member may be used as the closed tip portion 10, and welded integrally to the electrode 50. Alternately, one end portion of the hollow electrode 50 may be processed into a pointed end member. As the closed tip portion 10 and the hollow electrode 50 are to be pierced and inserted into the subcutaneous living tissue 200, they must be formed of an appropriate material in consideration of rigidity and biocompatibility, e.g. a stainless steel tube.

In addition, most of the length of the electrode 50 is covered with an insulation coating or rubber tube to form the insulating region 24. Therefore, although an RF current is applied via the electrode 50, the RF current is applied merely to the non-insulating region 20, and not applied to the living tissue 200 which is in contact with the insulating region 24. Also, the temperature sensor line 40 is inserted into the saline solution tube 30 to sense a temperature inside the closed tip portion 10 and the non-insulating region 20 of the hollow electrode 50 in a real time and use the same for RF output control. Since the saline solution discharge hole 22 formed by the laser is very small, a pressure of the saline solution discharged to the inside of the living tissue 200 via the hole 22 can be controlled not to damage the tissue in the body and not to exceed the allowable flow rate of the saline solution infused into the body during an operation.

Figure 4:
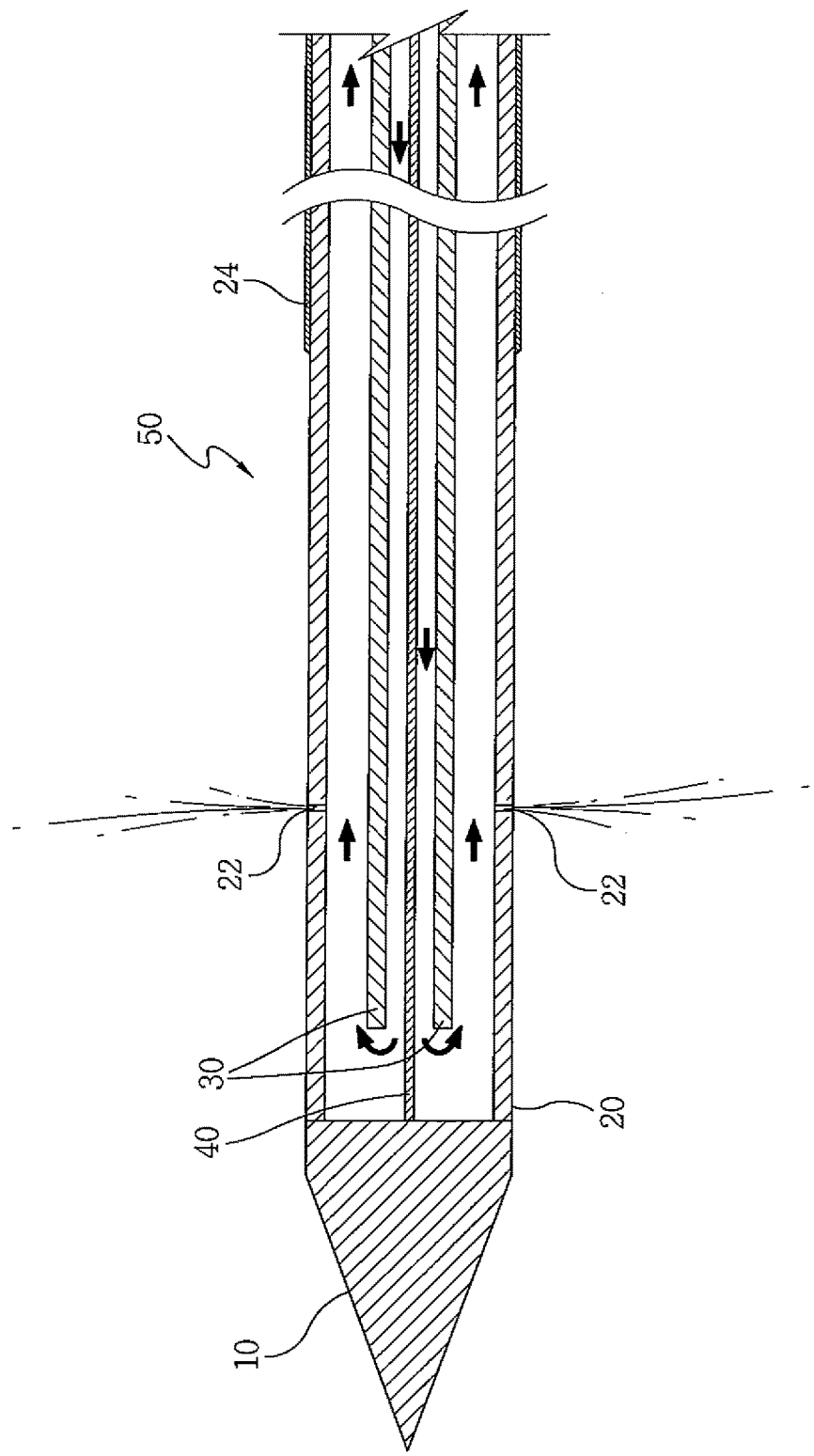
FIG. 4 is a sectional view illustrating an electrode for electrosurgery which is the present invention.

FIG. 4 is a sectional view illustrating the hollow electrode 50 for electrosurgery which is the present invention, i.e. an assembly state of the components explained with reference to FIG. 3. When the pressurized saline solution is introduced from the supply duct 82 explained in FIG. 2 to the saline solution tube 30, the pressurized saline solution cools the closed tip portion 10 and the non-insulating region 20 of the hollow electrode 50 via the saline solution tube 30. The saline solution discharged from the saline solution tube 30 is mostly discharged from the hollow electrode 50 through the discharge duct 84 via a space between the saline solution tube 30 and an inner surface of the hollow electrode 50. In the present invention, such a flow of the pressurized saline solution is defined as 'Circulation of saline solution'.

In the meantime, the present invention is characterized in that only some of the circulating saline solution is discharged to the outside of the hollow electrode 50 via the saline solution discharge hole 22. FIG. 4 schematically shows the saline solution discharged via the saline solution discharge holes 22, in a state where the hollow electrode 50 is positioned in the air and the pressurized saline solution is circulated under the operation conditions. Although the pressurized saline solution is emitted, since the saline solution discharge holes 22 formed by the laser have a very small size, the pressure and flow rate of the saline solution are restricted not to damage the living tissue 200 or body. It will be described later.

Figure 5:
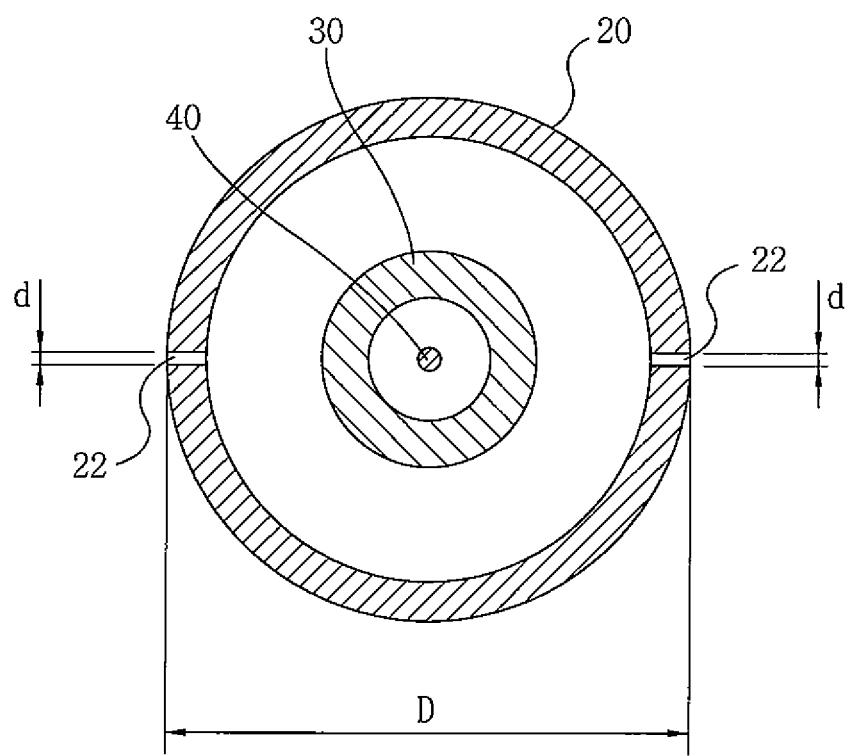
FIG. 5 is a sectional view illustrating the electrode for electrosurgery which is the present invention, when seen from a different angle.

FIG. 5 is a sectional view illustrating the electrode for electrosurgery which is the present invention, when seen from a different angle. When the hole 22 is bored in the non-insulating region 20 of the hollow electrode 50, the number of the holes 22 is not limited. However, if one hole 22 is bored, since the saline solution is discharged to one direction, an external force may be applied to the hollow electrode 50 due to a reaction. Such an external force may prevent the hollow electrode 50 from being located in an exact point of a target tumor tissue. Therefore, preferably, the holes 22 are formed in positions symmetrical about a center of the hollow electrode 50. As shown in FIG. 5, two circular holes 22 having the same diameter d are positioned spaced apart from each other at 180°. However, the number of the holes 22 is nothing but an example. If the number of the holes 22 is n, when the adjacent holes 22 are spaced apart at 360/n °, respectively, the sum of the external forces applied to the hollow electrode 50 due to a reaction is zero in the entire holes 22. It is thus possible to relatively easily locate the hollow electrode 50 in the exact point of the target tumor tissue.

Embodiments

An experiment object was a cow's liver, and an RF generator was a product of Valleylab. In these experiments, the saline solution discharge holes 22 were provided in the hollow electrode 50, spaced apart from each other at 180°. Experiment results of Embodiments 1 to 7 changing the size of the holes 22 were shown in the following Tables 1 to 3.

TABLE 1

| Embodiments | Hole radius (mm) | Hole number | Total circulation flow rate | Total hole area (mm²) |
|---|---|---|---|---|
| 1 | 0.01 | 2 | 90 cc/min | 0.000628 |
| 2 | 0.0125 | 2 | 90 cc/min | 0.0009813 |
| 3 | 0.015 | 2 | 90 cc/min | 0.001413 |
| 4 | 0.0175 | 2 | 90 cc/min | 0.0019233 |
| 5 | 0.02 | 2 | 90 cc/min | 0.002512 |
| 6 | 0.0225 | 2 | 90 cc/min | 0.0031793 |
| 7 | 0.025 | 2 | 90 cc/min | 0.003925 |

'Hole radius' represents the radius of each hole 22 bored by the laser. As described above, the holes 22 were formed in positions spaced apart from each other at 180°. The area of the two holes 22 and the total circulation flow rate of the pressurized saline solution were as shown in the above Table 1.

TABLE 2

| Embodiments | Leakage flow rate in air | Ratio of leakage flow rate to total circulation flow rate (%) | Discharge flow rate in tissue | Ratio of discharge flow rate to total circulation flow rate (%) | Discharge flow rate to leakage flow rate (%) |
|---|---|---|---|---|---|
| 1 | 0.31 cc/min | 0.344444444 | 0.25 cc/min | 0.277777778 | 80.6451612 |
| 2 | 0.82 cc/min | 0.911111111 | 0.66 cc/min | 0.733333333 | 80.4878048 |
| 3 | 1.21 cc/min | 1.344444444 | 0.97 cc/min | 1.077777778 | 80.1652892 |
| 4 | 1.65 cc/min | 1.833333333 | 1.35 cc/min | 1.5 | 81.8181818 |
| 5 | 2.20 cc/min | 2.444444444 | 1.81 cc/min | 2.011111111 | 82.2727272 |
| 6 | 2.75 cc/min | 3.055555556 | 2.42 cc/min | 2.688888889 | 88 |
| 7 | 3.42 cc/min | 3.8 | 2.95 cc/min | 3.277777778 | 86.2573099 |

Table 2 shows the leakage flow rate in the air and the discharge flow rate in the tissue via the holes 22, when the total circulation flow rate as shown in Table 1 was applied to the hollow electrode 50 with the above construction. In addition, Table 2 shows the ratio of the leakage flow rate in the air to the total circulation flow rate, the ratio of the discharge flow rate in the tissue to the total circulation flow rate, and the ratio of the discharge flow rate in the tissue to the leakage flow rate in the air.

TABLE 3

| Embodiments | Ablation necrosis time | Ablation volume (cm³) | Length of non-insulating region | Remarks |
|---|---|---|---|---|
| 1 | 3 min. | 10.65 | 1 cm | Good (small ablation volume) |
| 2 | 15 min. | 60.65 | 3 cm | Good |
| 3 | 15 min. | 151.42 | 3 cm | Good |
| 4 | 15 min. | 181.50 | 3 cm | Good |
| 5 | 15 min. | 208.57 | 3 cm | Good (a little irregular) |
| 6 | 15 min. | 238.14 | 3 cm | Good (a little irregular) |
| 7 | 15 min. | 274.63 | 3 cm | Good (a little irregular) |

Table 3 shows the ablation necrosis time and the ablation volume in the cow's liver tissue, and the length of the non-insulating region 22 of the electrode 50.

Considering the volume of the ablation necrosis region and irregularity of the spherical shape in the above embodiments, Embodiments 2, 3 and 4 were deemed to be optimum results. In the case of Embodiment 1, although the ablation volume was small because of a small discharge flow rate of saline solution, as discussed later, if the number of the holes 22 increases or the total circulation flow rate increases, a satisfactory result is expected. Meanwhile, although the ablation necrosis volume was larger in Embodiments 5, 6 and 7 than the previous embodiments, a sectional shape of the sphere was a little irregular or similar to an ellipse.

However, since the saline solution discharge holes 22 were very small, in any of the embodiments, the living tissue was not damaged by the discharged saline solution, and the discharge flow rate of the saline solution was not excessive. Generally, an allowable flow rate of saline solution infused into the body during the electrosurgery is 120 cc/hr. In the case of Embodiment 7 having the largest discharge flow rate of the saline solution among the embodiments of the present invention, the discharge flow rate of the saline solution was 44.25 cc(ml) in the experiment of 15 min. (38.85 cc(ml) in the tissue), satisfying the standard. Accordingly, the entire embodiments of the present invention were satisfactory in terms of the flow rate of the saline solution discharged to the inside of the body. Moreover, when an RF output applied to the electrode 50 is strong, since the discharged saline solution can be easily vaporized, it less affects the body.

It can be known from the above embodiments that the ratio of the leakage flow rate of the saline solution discharged via the saline solution discharge holes 22, i.e. the leakage flow rate in the air is less than 5%. That is, most of the saline solution performs the circulation process, and less than 5% of the circulating saline solution is discharged to the outside of the hollow electrode 50. The saline solution discharged at this flow rate is not harmful to the living tissue 200. That is, the possible circulation flow rate of the pressurized saline solution in the present invention is maximum 120 cc/min. When the leakage flow rate in the air is 5%, the flow rate of the saline solution leaked to the air for 15 minutes of the operation is 90 cc(ml) (the flow rate in the tissue is less than that), which satisfies the standard. As confirmed in the table, preferably, 0.3 to 3.8% of the pressurized saline solution circulating in the hollow electrode 50 can be discharged to the air, and more preferably, 0.9 to 2.0% of the pressurized saline solution circulating in the hollow electrode 50 can be discharged to the air. In this case, as revealed in Embodiments 2, 3 and 4 of the present invention, it was possible to obtain an ablation necrosis region of a satisfactory spherical shape.

In these experiments, the flow rate of the liquid discharged to the cow's liver via the holes 22 was about 80 to 88% of the flow rate of the pressurized saline solution leaked to the air, and the leakage flow rate in the air and the discharge flow rate in the tissue had an almost linear relation.

When the radius of the saline solution discharge hole 22 was 0.01 mm, the ablation size did not increase regardless of time. Therefore, in order to increase the ablation volume, preferably, the flow rate of the saline solution discharged to the inside of the tissue exceeds 0.25 cc/min., i.e., the flow rate of the saline solution leaked to the air exceeds 0.31 cc/min. When the radius of the saline solution discharge hole 22 is so small that the flow rate of the saline solution leaked to the air is less than 0.31 cc/min., since the flow rate of the saline solution is too small to normally perform cooling and lower an impedance, the volume of the ablated tissue becomes small. However, although the holes 22 are small as in Embodiment 1 having a radius of 0.01 mm, the number of the holes 22 may be increased to improve the flow rate. Accordingly, when two holes 22 are formed as in Embodiment 1, the flow rate is deficient. But, if a plurality of holes having a radius of Embodiment 1 are bored in symmetrical positions, it is possible to discharge the saline solution sufficient to lower the impedance of the living tissue 200. That is, if the number of the holes 22 can be increased without affecting rigidity of the hollow electrode 50, even though the area or diameter of each hole 22 is small, there is no difficulty in performing an operation.

Alternately, in a state where the hollow electrode 50 is exposed in the air, when the saline solution circulates in the electrode 50 at 90 cc/min., if the flow rate of the saline solution discharged to the air via the saline solution discharge hole 22 ranges from 0.82 to 1.65 cc/min., or if the radius of the saline solution discharge hole 22 ranges from 0.0125 to 0.0175 mm, it is possible to obtain an ablation necrosis region of a desirable spherical shape as suggested in Embodiments 2, 3 and 4.

Next, in the cases of Comparative example 1 which supplies saline solution to the inside of a hollow electrode, and discharges the entire supplied saline solution to the inside of a tissue outside the hollow electrode via a porous body formed around a tip portion of the electrode, and Comparative example 2 which cools a hollow electrode by saline solution circulation that introduces saline solution into the inside of the electrode through the inside of a saline solution tube installed in the electrode, makes the saline solution exchange heat in the electrode, and collects the saline solution through a space between the saline solution tube and the electrode, an ablation volume did not exceed 30 $cm_3$ in most experiments. However, according to the present invention, as shown in Table 3, when the radius of the hole 22 increased, the ablation volume increased more than that of Comparative examples 1 and 2 by at least 2 to 9 times.

When saline solution is used as pressurized saline solution, high concentration (e.g. over 3%) saline solution and 0.9% physiologic saline solution can be used. Since the 0.9% physiologic saline solution has a lower concentration than the high concentration saline solution, it less improves electric conductivity but obtains a more even ablation shape. These experiments were performed using the 0.9% physiologic saline solution as saline solution. It is expected that the high concentration saline solution which has an excellent effect in improving electric conductivity of the living tissue can more increase the ablation volume.

In addition, in these experiments, the circulation flow rate of the saline solution was 90 cc/min. If the circulation flow rate of the saline solution is equal to or less than 70 cc/min. in the electrode having a diameter of 1.5 mm, the flow rate of the saline solution is too small to manifest an appropriate cooling effect and obtain an appropriate ablation size. Moreover, the circulation flow rate of the saline solution cannot exceed 120 cc/min. because of a technical limit. When the circulation flow rate of the saline solution exceeds 120 cc/min., overcoming the technical limit, the cooling effect of the electrode improves. However, since the flow rate of the saline solution discharged to the inside of the tissue increases with the increase of the total circulation flow rate, there is a disadvantage in that the tissue is irregularly ablated. Accordingly, preferably, the more the circulation flow rate increases, the smaller the size of the hole should be so as to reduce the flow rate discharged to the inside of the tissue.

What is claimed is:

1. An electrode for an electrosurgical unit, comprising:
a conductive hollow electrode formed in an elongated hollow tube shape, wherein a diameter of the hollow electrode ranges from about 1.2 mm to 3.0 mm, and the hollow electrode includes a non-insulating region of a predetermined length formed on one side of the hollow electrode, an insulating region formed on an outer surface of the hollow electrode in an area other than the non-insulating region, and a closed-tip portion extending distally from the non-insulating region of the hollow electrode;
a saline solution circulation structure that is configured to supply pressurized saline solution for cooling the non-insulating region and a living tissue which is in contact with the hollow electrode, wherein a circulation flow rate of the pressurized saline solution is more than 70 cc/min, the saline solution circulation structure includes the hollow electrode having an electrode handle, a saline solution tube located in the hollow electrode, a supply duct configured to pass the pressurized saline solution through the electrode handle from the outside of a living body to the inside of the hollow electrode, and a discharge duct configured to discharge the pressurized saline solution through the electrode handle from the inside of the hollow electrode to the outside of the living body, wherein the pressurized saline solution is circulated by being supplied through the supply duct from the outside of the living body to the inside of the hollow electrode, where heat exchange occurs, and discharged through the discharge duct from the inside of the hollow electrode to the outside of the living body; and one or more saline solution discharge holes formed in the non-insulating region of the hollow electrode configured to directly discharge some of the circulating pressurized saline solution to the living tissue which is in contact with the hollow electrode, wherein the one or more saline solution discharge holes are micro holes each having a radius in the range of about 0.01 to 0.025 mm, and the one or more saline solution discharge holes are laser-bored holes, and in a state in which the hollow electrode is exposed in air, when the pressurized saline solution circulates in the electrode at about 90 cc/min, the flow rate of the pressurized saline solution discharged to the air via the one or more saline solution discharge holes ranges from about 0.31 to 3.42 cc/min.

2. The electrode of claim 1, wherein the one or more saline solution discharge holes comprise a plurality of the saline solution discharge holes formed in a plural number of positions symmetrical about the hollow electrode.

3. The electrode of claim 1, wherein, in a state where the hollow electrode is exposed in the air, less than 5% of the pressurized saline solution circulating in the hollow electrode is discharged to the air via the one or more saline solution discharge holes.

4. The electrode of claim 3, wherein, in a state where the hollow electrode is exposed in the air, 0.3 to 3.8% of the pressurized saline solution circulating in the hollow electrode is discharged to the air via the one or more saline solution discharge holes.

5. The electrode of claim 4, wherein, in a state where the hollow electrode is exposed in the air, 0.9 to 2.0% of the pressurized saline solution circulating in the hollow electrode is discharged to the air via the one or more saline solution discharge holes.

6. The electrode of claim 1, wherein, in a state where the hollow electrode is exposed in the air, when the saline solution circulates in the electrode at 90 cc/min., the flow rate of the saline solution discharged to the air via the one or more saline solution discharge holes ranges from 0.82 to 1.65 cc/min.

7. The electrode of claim 1, wherein the radius of the one or more saline solution discharge holes ranges from 0.0125 to 0.0175 mm.

8. The electrode of claim 1, wherein the pressurized saline solution is pressurized to 700 to 1060 KPa, and supplied to the inside of the hollow electrode.

* * * * *